United States Patent [19]
Anzalone

[11] Patent Number: 5,866,600
[45] Date of Patent: Feb. 2, 1999

[54] METHOD FOR TREATING AN INFLAMMATORY CONDITION WITH PREVENTION OF SECRETIVE ACTIVITY OF GASTRIC SECRETIVE LEVEL

[75] Inventor: Sergio Anzalone, Rome, Italy

[73] Assignee: Medosan Ricerca S.R.L., Cecchina, Italy

[21] Appl. No.: 679,807

[22] Filed: Jul. 15, 1996

[30] Foreign Application Priority Data

Jul. 14, 1995 [IT] Italy .................................. RM95A0484

[51] Int. Cl.[6] ..................................................... A61K 31/40
[52] U.S. Cl. ............................................................ 514/423
[58] Field of Search ............................................. 514/423

[56] References Cited

U.S. PATENT DOCUMENTS 4,578,481  3/1986  Baglioni .
4,882,349  11/1989  Baglioni .................................. 514/423

OTHER PUBLICATIONS

Tubaro et al., "Studies on the gastric tolerability of the new non-sterodidal anti-inflammatory drug amtolmetin guacyl", Arzneimittel-Forschung 45(12), pp. 1298-1302 abstract only, Dec. 1995.
A. Caruso et al, "Pharmacological properties and toxicology of MED-15, a prodrug of tolmetin", Durgs under Experimental and Clinical Research, vol. 18, NO. 11/12, pp. 481-485 (1995).

*Primary Examiner*—Raymond Henley, III
*Attorney, Agent, or Firm*—Browdy and Neimark

[57] ABSTRACT

A method for treating an inflammatory pathological condition with simultaneous prevention of a secretive activity on gastric secretion comprising the step of administering a subject in need thereof an effective amount of 2-methoxyphenyl-1-methyl-5p-methylbenzoyl-pyrrol-2acetamido acetate.

1 Claim, No Drawings

METHOD FOR TREATING AN INFLAMMATORY CONDITION WITH PREVENTION OF SECRETIVE ACTIVITY OF GASTRIC SECRETIVE LEVEL

DESCRIPTION

The present invention relates to the use of the compound 2-methoxyphenyl-1-methyl-5p-methylbenzoyl-pyrrol-2-acetamido acetate (known also as amtolmetin guacyl) for the production of non-steroidal anti-inflammatory drugs with simultaneous antisecretory activity on gastric secretion.

State of the art

Non-steroidal anti-inflammatory drugs (NSAIDs) have been used for many years in therapy. It is also well known that NSAIDs produce lesions to gastrointestinal apparatus depending on the length of the treatment and on the type of drug. This problem has a dramatic importance in cases where the therapy must be protracted for a long time. An example is rheumatoid arthritis in old people, where a chronic treatment is needed to keep under control the inflammatory state and the pain and make acceptable the quality of life.

At present there is a pharmacologic dogma establishing a mandatory connection between anti-inflammatory effect and gastric lesions. This dogma has been recently shaken by the availability of newly synthetized anti-inflammatory drugs showing gastrolesive effects lower than those of old ones. Notwithstanding that equiactive doses of drug could produce lesions of different seriousness, it was settled that an anti-inflammatory drug showed, in any case, a gastrolesive effect. From this fact it followed that it could not be expected that these drugs known in the art could show a gastroprotective effect.

It has been now surprisingly found that the compound 2-methoxyphenyl-1-methyl-5p-methylbenzoyl-pyrrol-2-acetamido acetate, which is an effective anti-inflammatory non-steroidal drug as already known in the art, shows a remarkable antisecretory activity on gastric secretion in mammals.

The compound 2-methoxyphenyl-1-methyl-5p-methylbenzoyl-pyrrol-2-acetamido acetate (known also as amtolmetin guacyl) is already known in the art and is for instance disclosed in Italian patent application no. 47881A/82 and in U.S. Pat. No. 4,578,481 issued on Mar. 25, 1986.

Both the documents of the state of the art disclose that the above compound shows anti-inflammatory, analgesic, antipyretic, antitussive and antisecretive (on the mucus of the respiratory airway) properties. No mention, either direct or indirect, is made about a possible antisecretive effect on the gastric secretion in mammals.

It is therefore the subject matter of the present invention: a method for treating an inflammatory pathological condition with simultaneous prevention of a secretive activity on gastric secretion comprising the step of administering a subject in need thereof an effective amount of 2-methoxyphenyl-1-methyl-5p-methylbenzoyl-pyrrol-2acetamido acetate.

While the production and characterisation of the compound of the present invention are disclosed in the above mentioned documents which are hereby incorporated for reference, in the following the results of pharmacologic tests showing the antisecretive activity of the above compound are listed.

Chemicals and animals used

The following substances have been used: carboxymethylcellulose sodium, histamine dichloride, piroxicam, carrageenin and acetylcholine chloride produced by Sigma Chimica (Milano, Italy); cimetidine produced by Farchemia (Milano, Italy); 2-methoxyphenyl-1-methyl-5p-methylbenzoyl-pyrrol-2-acetamido acetate and naproxen produced by Alfa Chemicals Italiana (Bergamo, Italia); diclofenac sodium, nimesulide and tolmetin produced by LCM Trading (Milano, Italy); gastrin produced by Fluka Chimica (Milano, Italy). Male Wistar rats, 250±10 g b.w. (Charles River, Calco, Como, Italy), quarantined for five days prior to the beginning of the trial and divided into groups of 3 animals per cage, were used for determination of gastric lesions and of $ID_{50}$ determination. Immature male Wistar rats, 30–45 g b.w.(Harlan Nossan, Milano) were used for the determination of the antisecretory effect on isolated rat stomach. The guinea-pigs used were the Dunkin Hartley guinea-pigs (Harlan Nossan, Milano, Italy).

The animals were fed standard laboratory chow with free access to water under animal house conditions of 22±2° C. temperature, relative humidity 55±10% and 12-h light-dark cycle.

Determination of gastric lesions

In this first test the effect of the compound 2-methoxyphenyl-1-methyl-5p-methylbenzoyl-pyrrol-2-acetamido acetate and of some reference NSAIDs (diclofenac sodium, naproxene, nimesulide, piroxicam and tolmetin) on the gastric mucosa of rat after repeated oral administration in order to test the existence and extent of the gastric lesions, has been verified.

The animals entered in the trial, randomized and divided into groups of 6 rats each, were fasted for 16 h prior to treatment, with access to water ad libitum. They were re-fed 1 h after drug adminisration. The compound 2-methoxyphenyl-1-methyl-5p-methylbenzoyl-pyrrol-2-acetamido acetate and the other reference NSAIDs, suspended in 1% carboxymethylcellulose (CMC) solution, were orally administered by gastric gavage in a volume of 6 ml/kg for four consecutive days. Controls received the vehicle in the same way as the treated animals. 4 h after the last administration the animals were killed by ether overdose; the stomachs were removed, rinsed with 10 ml of saline and immersed in 1% formalin. They were later opened along the greater curvature and the mucosa examined for lesions.

The seriousness of the lesion was quantified according to a scale graduated from 1 to 3 according to the size of the lesions: 1=ulcer<1 mm; 2=ulcer 1–2 mm; 3=ulcer>2 mm. The total sum was divided by 10 to obtain the "erosion index". The gastric lesions were evaluated by two independent investigators under blind conditions according to Main & Whittle method (BU. Pharmac 1975:53; p. 217–224).

Since pharmacologic studies in carrageenin-induced paw oedema in rat show that a daily 50 mg/kg dose in oral administration of 2-methoxyphenyl-1-methyl-5p-methylbenzoyl-pyrrol-2-acetamido acetate is higly efficacious as anti-inflammatory agent, this daily dose has been selected for the evaluation of the gastric lesions of same compound. Since the average daily dose in man (for the anti-inflammatory activity) is 600 mg, the comparative efficacious dose in the rat is in the ratio of 12:1. More precisely, comparative evaluation with the other NSAID compounds was calculated as follows:

600 mg/die: 50 mg/kg=daily dose of reference NSAID in man: X where X represents the daily dose of the reference NSAID in rat. This criterion keeps into account the "real" activity ratio in man. In this work the "ratio to rat dosage" has also been included which keeps into account ratios homogeneous to the same animal species. To evaluate the "ratio to rat dosage" the $ID_{50}$ has been determined using the carrageenin-induced oedema as inflammatory test. This made possible to determine in rat an equiactive dose which is, consequently, comparable among the various compared NSAIDS.

Determination of $ID_{50}$ $ID_{50}$, relative to the products under examination (considered in table 1), has been evaluated using the antiinflammatory response to carrageenin-induced paw oedema (according to Wong et al, J Pharmacol Exp, 1973:1855; pages 127–138). The products, suspended in 1% CMC, were administered orally in a total volume of 5 ml/rat. 1 h later, 0.1 ml of 1% carrageenin sterile solution was injected into the hind subplantar aponeurosis. Volume of the paw was measured immediately prior to injection of the phlogogen and 2 h thereafter, by means of a plethysmograph. The percentage of inhibition of oedema was calculated as follows:

$$1 - \Delta V \text{ treated}/\Delta V \text{ control} \times 100$$

where $\Delta V$=final V−initial V.

Three doses have been used for each NSAID and the $ID_{50}$, which indicates the quantity in mg/kg inhibiting oedema by 50%, has been determined.

The results are listed in the following table 1, where each expressed value is the average of 6 determinations. In this table the results either of the so-called "ratio to human dosage" and of the "ratio to rat dosage" are listed.

TABLE 1

| Active principle | Ratio to human dosage (mg/kg) | Gastric lesion index | Ratio to rat dosage (mg/kg) ($ID_{50}$ mg/kg × 5) | Gastric lesion index |
|---|---|---|---|---|
| Controls | — | 1.00 | — | 1.00 |
| amtolmetin guacyl | 50.0 | 1.00 | 100.0 (double dose) | 1.00 |
| Diclofenac sodium | 7.5 | 68.12* | 15.8 | 63.7 |
| Naproxen | 37.5** | 273.5*** | 34.0 | 283.7 |
| Nimesulide | 16.6 | 21.25 | 28.5 | 46.2 |
| Piroxicam | 2.0 | 31.25 | 13.8 | 176.2 |
| Tolmetin | — | — | 61.2# | 79.7 |

*Diffuse haemorrhagic gastritis was also present
**Naproxen was taken at the lowest dosage used in man (450 mg/day)
***One animal died after the third treatment and two showed extremely thin stomach walls
Tolmetin was administered at an equimolar dose compared to amtolmetin guacyl The above table shows that, with respect to reference NSAIDs, amtolmetin guacyl does not have gastrolesive effects.

TABLE 2

| Groups | Dose (mg/kg) | Rats with lesions/ rats used | Erosion index ± E.S. | Gastric lesion index |
|---|---|---|---|---|
| Controls | — | 2/6 | 0.066 ± 0.042 | 1.00 |
| amtolmetin guacyl | 200 | 2/6 | 0.066 ± 0.049 | 1.00 |

The previous table shows that amtolmetin guacyl does not have a gastrolesive potential different from that of the controls even when the dose is at extremely high levels outside the therapeutical range of use.

In the following table 3 the results of a histological evaluation, in comparison with the controls, of the effect of repeated administrations of amtolmetin guacyl and of two -reference drugs are reported. The evaluation has been carried out under double blind conditions. The rats were treated with amtolmetin guacyl (oral administration 100 mg/kg), diclofenac (15.8 mg/kg) and tolmetin (61.2 mg/kg) in 1% CMC for 4 consecutive days. The controls received only the vehicle in oral administration. 4 h after the last administration the animals were killed by ether overdose and the stomachs removed, rinsed with saline and immersed in 1% formalin solution. The results confirm the lack of gastrolesive effects.

TABLE 3

| Animal No. | Drug | Macroscopic findings | Histology |
|---|---|---|---|
| 1 | tolmetin | 1 ulcer of the corpus | ulcerous lesion of mucosa involving entire mucosal thickness |
| 2 | = | normal | negative |
| 3 | = | 8 small ulcers | >1 mm areas of cellular necrosis extending through two-thirds of the mucosa (surface epithelium, region of mucus neck cells and of parietal cells) |
| 4 | = | 2 ulcers of the corpus | ulcerous lesion of mucosa as in 1 |
| 5 | = | multiple dark lesions | >1 mm areas of cellular necrosis extending through two-thirds of the mucosa (surface epithelium, region of mucus neck cells and of parietal cells) |
| 6 | = | normal | negative |
| 7 | amtolmetin guacyl | normal | negative |
| 8 | = | normal | negative |
| 9 | = | normal | negative |
| 10 | = | normal | negative |
| 11 | = | normal | negative |
| 12 | = | normal | negative |
| 13 | controls | normal | 2 lesions as in 3 |
| 14 | = | normal | negative |
| 15 | = | normal | negative |
| 16,17 | diclofenac | tiny ulcers | 2 lesions as in 3 |
| 18,19 | = | mucosal ulcers | multiple areas of coagulative necrosis extending through two-thirds of the mucosa |
| 20,21 | = | normal | negative |

Determination of antisecretory effect in vitro on gastric secretion

In the following the results of pharmacologic tests showing the antisecretorry effect of amtolmetin guacyl are reported.

The methods used were those according to Boughton-Smith & Whittle (Br J Pharmac 1981:72; pages 291–298), Bunce & Parson (J Physiol 1976:258; pages 453–465) and Bunce, Parson & Rollings(Br J Pharmac 1976:58; pages 149–156). The stomach of the rat, which was killed by cervical dislocation, was removed after having ligated the oesophagus. An incision was made in the forestomach through which a polyethylene cannula was inserted and tied; a second cannula was inserted through the pyloric sphincter. The stomach was flushed with 10–20 ml of warm Krebs-Henselheit solution (mucosal solution). The stomach, in a 100 ml organ bath containing the Krebs-Henselheit solution (serosal solution) at 37° C., was perfused at a flow of of 1 ml/min with the mucosal solution.

The serosal solution, gassed with 95% $O_2$ and 5% $CO_2$, was composed of the following (mM): NaCl 119.0; KCl 4.7; $MgSO_4$ 1.2; glucose 5.6; $CaCl_2$ 1.0; $NaHCO_3$ 30.0; $KH_2PO_4$ 0.5 (for histamine) and NaCl 119.0; KCl 4.7; $MgSO_4$ 1.2; glucose 5.6; $CaCl_2$ 2.5; $NaHCO_3$ 25.0; $KH_2PO_4$ 1.03 (for acetylcholine and gastrin).

The mucosal solution, gassed with $O_2$ (100%) was of the same composition but without the buffer salts. The perfusate was collected every 15 minutes and titred to pH 7.0 with NaOH $10^{-3}$ m: acid secretion is expressed in nmol/min. Basal acid secretion was allowed to plateau before testing for acid secretion response to histamine, acetylcholine and gastrin; then agonist and antagonist were introduced into the serosal solution, in a volume not exceeding 100 μl each. The secretory response (Δ acid) was calculated as the quantity of HCl secreted at the peak minus the quantity at basal level at the introduction of the agonist. The antisecretory activity of amtolmetin guacyl at concentrations of $10^{-5}$ and $10^{-4}$M in DMSO, after incubation in the serosal solution for 30 minutes prior to addition of histamine ($10^{-3}$ and $10^{-4}$M ), acetylcholine ($10^{-3}$M) or gastrin ($6\times10^{-7}$M) was tested. The acid secretion was recorded for 45 minutes after the introduction of the agonists. In the same way the effect of cimetidine (used in view of the fact of being a known antiulcer drug) at concentration of $10^{-4}$M, using histamine as agonist, was tested. Its effect against the other agonists, as known from scientific literature, is null.

The following table 4 lists the results showing the effectiveness of amtolmetin guacyl on gastric secretion in the above described tests.

TABLE 4

| Animal No. | Agonist M | Δ Acid nMol/min | Animal No. | Antagonist M | Δ Acid nMol/min |
|---|---|---|---|---|---|
| 23 | histamine $10^{-4}$ | 51.3 ± 6.4 | 11 | amtolmetin guacyl $10^{-4}$ | 19.2 ± 5.4 |
|  |  |  | 6 | amtolmetin guacyl $10^{-5}$ | 16.1 ± 5.4 |
| 7 | histamine $10^{-3}$ | 42.3 ± 4.9 | 5 | amtolmetin guacyl $10^{-4}$ | 17.9 ± 2.1 |
| 8 | histamine $10^{-4}$ | 67.0 ± 17.8 | 5 | cimetidine $10^{-4}$ | 14.3 ± 7.2 |
| 6 | acetylcholine $10^{-3}$ | 90.2 ± 6.5 | 6 | amtolmetin guacyl $10^{-4}$ | 71.2 ± 5.4 |
| 10 | gastrin $6 \times 10^{-7}$ | 64.0 ± 5.6 | 6 | amtolmetin guacyl $10^{-4}$ | 30.7 ± 3.7 |

The results are expressed as average ±E.S. The comparison with cimetidine, known antiulcer drug, with similar values is a further confirmation of the effectiveness of the antisecretory activity of amtolmetin guacyl.

Antisecretory activity in vivo in rat

The methods used were those described by G Coruzzi, M. Adami, C. Pozzoli, E. Poli, G. Bertaccini (Pharmacology 1994;48: pages 69–76) and M. Leitold, W. Fleissig and A. Merk (Arzneim-Forsch/Drug Res. 34(I), Nov. 4, 1984).

The animals were treated in oral administration with amtolmetin guacyl 15, 50 or 100 mg/kg, 1 h before the beginning of the perfusion with histamine. The controls received only the vehicle (CMC 1%).

After anaesthesia with urethan (1.25 g/kg i.p.), the oesophagus was ligated close to the stomach. Two cannulas of polyethylene are then inserted: one was inserted in the forestomach, the second one was inserted directly into the pyloric sphincter. The stomach was flushed with saline at 37° C. (1 ml/min) and the flushed liquid, collected every 15 minutes, titred at ph 7 with NaOH $10^{-2}$M. The acid secretion was induced by an intravenous infusion (0.1 ml/min) of histamine (30 μmol/kg/h). The acidity is expressed as μEqH$^+$/15 min. The results are listed in the following table 5.

TABLE 5

Antisecretory activity of amtolmetin guacyl in rat

| Time (min) | amtolmetin guacyl 50 mg/kg | P ≤ | amtolmetin guacyl 100 mg/kg | P ≤ | Controls |
|---|---|---|---|---|---|
| 0 | 4 | — | 9 | — | 10 |
| 15 | 4 | n.s. | 8 | n.s. | 12 |
| 30 | 5 | 0.05 | 10 | 0.05 | 22 |
| 45 | 11 | 0.05 | 11 | 0.05 | 36 |
| 60 | 15 | 0.05 | 12 | 0.05 | 46 |
| 75 | 17 | 0.01 | 13 | 0.01 | 50 |
| 90 | 19 | 0.01 | 14 | 0.01 | 60 |
| 105 | 18.5 | 0.01 | 15 | 0.01 | 63 |
| 120 | 22 | 0.01 | 13 | 0.01 | 68 |
| 135 | 20 | 0.01 | 14 | 0.01 | 69 |

Therefore amtolmetin guacyl is suitable for an antiinflammatory treatment with antisecretory activity on gastric secretion with doses of 600 up to 1200 mg/day.

I claim:

1. A method for reducing gastric hydrochloric acid secretion in a patient in need thereof, comprising administering amtolmetin guacyl to said patient in an amount sufficient to simultaneously decrease gastric hydrochloric acid secretion and reduce pain and inflammation.

* * * * *